US00PP37205P2

(12) United States Plant Patent
McCracken

(10) Patent No.: US PP37,205 P2
(45) Date of Patent: Jan. 13, 2026

(54) ***CAREX* PLANT NAMED 'Lunar Falls'**

(50) Latin Name: ***Carex* hybrid**
Varietal Denomination: Lunar Falls

(71) Applicant: Thomas Patrick McCracken, Zebulon, NC (US)

(72) Inventor: Thomas Patrick McCracken, Zebulon, NC (US)

( * ) Notice: Subject to any disclaimer, the term of this patent is extended or adjusted under 35 U.S.C. 154(b) by 0 days.

(21) Appl. No.: 19/274,523

(22) Filed: Jul. 19, 2025

(51) Int. Cl.
*A01H 6/00* (2018.01)
*A01H 5/02* (2018.01)

(52) U.S. Cl.
USPC ..... Plt./384

(58) Field of Classification Search
USPC ..... Plt./384
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Carex* plant named 'Lunar Falls' that is characterized by its variegated foliage with wide white margins, its fast growing plant habit with a one-gallon plant produced in one season, its ease of propagation by division, and its very stable variegation with no solid white or green shoots observed.

2 Drawing Sheets

Botanical classification: *Carex* hybrid.
Varietal denomination: 'Lunar Falls'.

BACKGROUND OF THE INVENTION

The present invention relates to a new and distinct cultivar of *Carex* hybrid and will be referred to hereafter by its cultivar name, 'Lunar Falls'. 'Lunar Falls' is a new cultivar of perennial grown for container and landscape use.

The new cultivar was discovered by the Inventor in spring of 2020 as a naturally occurring cimeral mutation of *Carex* 'Feather Falls' (U.S. Plant Pat. No. 26,199) in a container in Zebulon, North Carolina.

Asexual propagation of the new cultivar was first accomplished by division by the Inventor in July of 2020 in Zebulon, North Carolina. Asexual propagation by division have determined that the characteristics are stable and are reproduced true to type in successive generations.

SUMMARY OF THE INVENTION

The following traits have been repeatedly observed and represent the characteristics of the new cultivar. These attributes in combination distinguish 'Lunar Falls' as a distinct cultivar of *Carex*.

1. 'Lunar Falls' exhibits variegated foliage with wide white margins.
2. 'Lunar Falls' exhibits a fast growing plant habit with a one-gallon plant produced in one season.
3. 'Lunar Falls' exhibits ease of propagation by division.
4. 'Lunar Falls' exhibits very stable variegation with no solid white or green shoots observed.

The parent plant of 'Lunar Falls' differs from 'Lunar Falls' in having thinner margins that are creamy white in color and a slower growth habit. 'Lunar Falls' can be most closely compared to *Carex* cultivars 'Everest' (U.S. Plant Pat. No. 20,955) and 'Everillo' (U.S. Plant Pat. No. 21,002). 'Everest' is similar to 'Lunar Falls' in having variegated foliage with white margins, long pendulous leaves, and a clumping growth habit. 'Everest' differs from 'Lunar Falls' in having variegated foliage with narrower white margins, less adaptability to growing conditions with less drought and sun tolerance, a smaller plant size and slower growth habit. 'Everillo' is similar to 'Lunar Falls' in having variegated foliage, long pendulous leaves, and a clumping plant habit. 'Everillo' differs from 'Lunar Falls' in having variegated foliage with golden colored margins, less adaptability to growing conditions with less drought and sun tolerance, and a smaller plant size.

BRIEF DESCRIPTION OF THE DRAWINGS

The accompanying color photographs illustrate the overall appearance and distinct characteristics of the new *Carex*. The plant in the photographs were taken of a one-year-old plant of the new cultivar as grown outdoors in 0.5-gallon containers in Zebulon, North Carolina.

The photograph in FIG. 1 provides a side view of the plant of 'Lunar Falls' in bloom.

Figure 1:
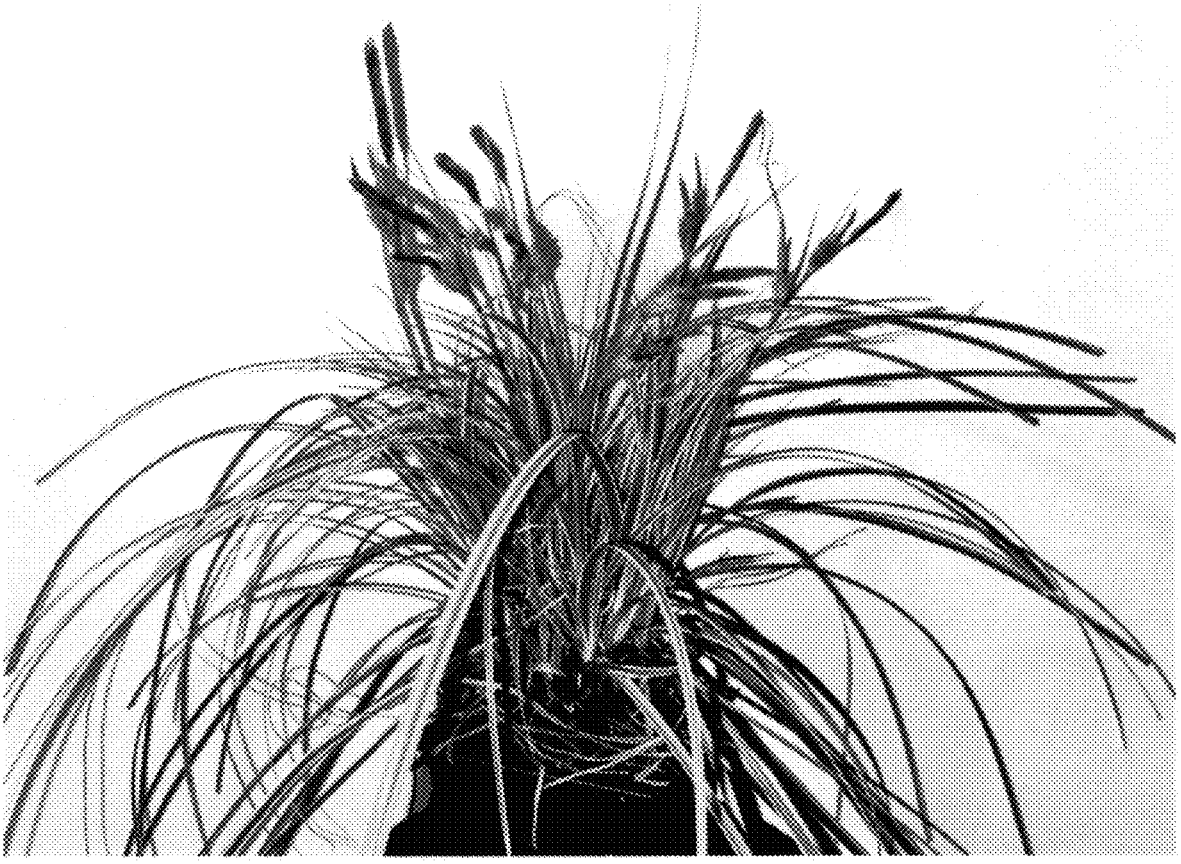
Figure 2:
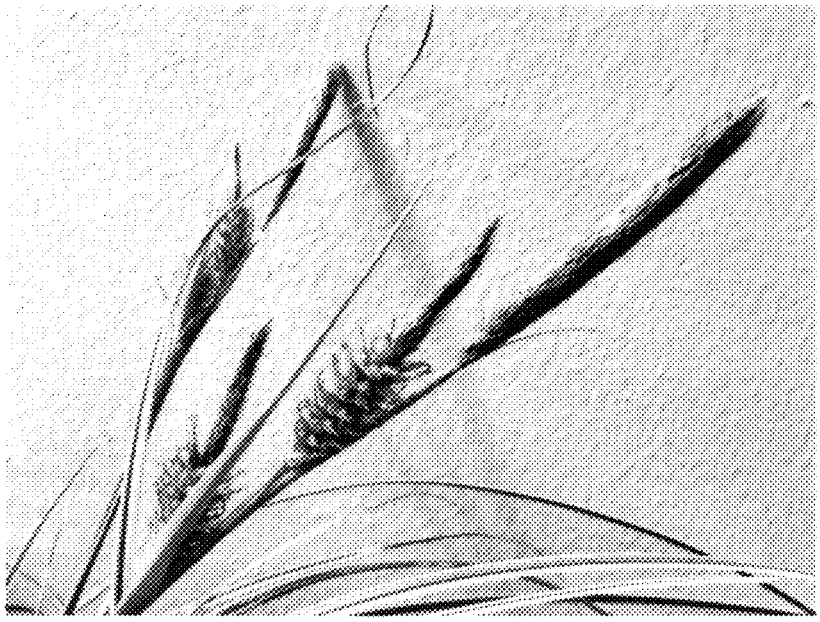

The photograph in FIG. 2 provides a close up of the inflorescences of 'Lunar Falls'.

Figure 3:
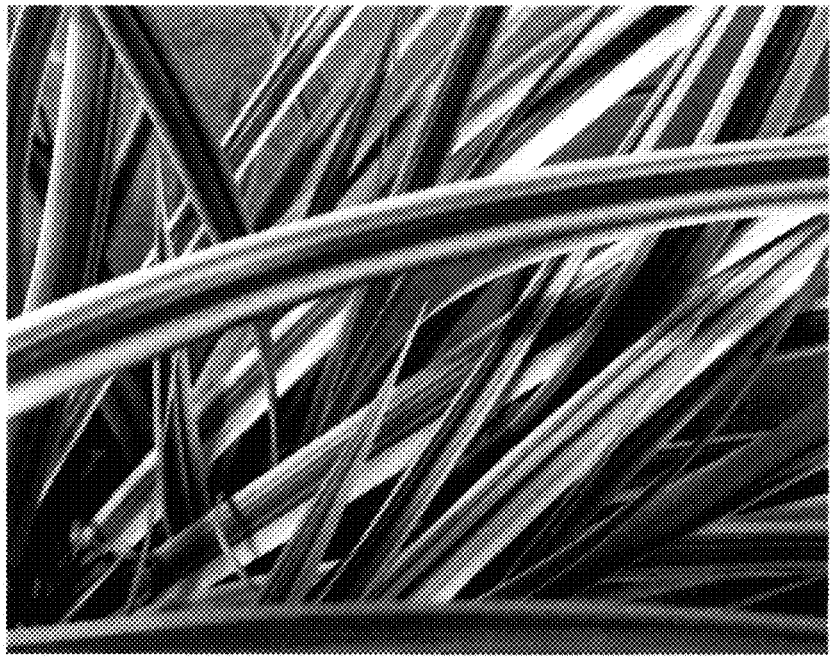

The photograph in FIG. 3 provides a close up of the foliage of 'Lunar Falls'. The colors in the photographs are as close as possible with the photographic and printing technology utilized and the color values cited in the detailed botanical description accurately describe the colors of the new *Carex*.

DETAILED BOTANICAL DESCRIPTION

The following is a detailed description of one-year-old plants of the new cultivar as grown outdoors in 0.5-gallon containers in Zebulon, North Carolina. The phenotype of the new cultivar may vary with variations in environmental, climatic, and cultural conditions, as it has not been tested under all possible environmental conditions. The color determination is in accordance with the 2015 Colour Chart of the Royal Horticultural Society, London, England, except where general color terms of ordinary dictionary significance are used.

General Description:

*Blooming period*.—2 to 3 weeks in early summer in North Carolina.

*Plant type*.—Herbaceous perennial.

*Plant habit*.—Upright with arching leaves.

*Growth habit*.—Upright, compact, clump forming, arching foliage.

*Height and spread*.—Average of 33 cm in height and 58 cm in diameter as a one-year-old plant grown in a container, reaches 61 cm in height and 1.2 m in spread in the landscape.

*Hardiness*.—At least in U.S.D.A. Zones 5 to 9.

*Diseases and pests*.—No susceptibility or resistance to pests and diseases has been oberved.

*Root description*.—Short, stout rhizomes with dense, fibrous roots, roots moderately branched, color; a blend of NN155D, 162C, and 176A.

*Propagation*.—Shoot division.

*Time required for root development*.—4 to 6 weeks to produce a well rooted liner from a division, will fully root in a one-gallon container in one growing season.

*Shoots*.—An average of 30 main shoots growing from the base.

*Growth rate*.—High.

Foliage Description:

*Leaf shape*.—Linear, curved.

*Leaf division*.—Simple.

*Leaf base*.—Sheathing.

*Leaf apex*.—Long acuminate.

*Leaf aspect*.—Average angle of 30° to 40° to shoot axis, leaves initially emerge upright, then cascade outward and finally arch downward.

*Leaf venation*.—Parallel, not distringuishable except main vein, color of upper and lower surface of main vein 144A.

*Leaf margins*.—Entire, sharp to the touch when rubbed due to very small teeth that are too small to be seen or measured.

*Leaf size*.—Average of 50 cm in length and 7 mm in width.

*Leaf number*.—Average of 15 leaves per shoot, 80 per plant.

*Leaf arrangement*.—Alternate.

*Leaf surface*.—Upper and lower surface smooth, glabrous, upper surface glossy, lower surface moderately glossy.

*Leaf color*.—Young and upper and lower surface; 144A, margins are thin and a blend of NN155D to NN155A, mature upper surface; narrow center stripe 141A, wider margins NN155D to NN155A, mature lower surface; wider center stripe 144A, narrow margins NN155D.

*Petiole*.—None.

*Leave sheathes*.—Average of 4 cm in length, 4 mm in width, transparent, 158B, laterally striped 200B.

Flower Description:

*General description*.—Terminal racemes, male and female flowers in separate spikelets.

*Inflorescence size*.—Averages 13 cm in height and 5 cm in width.

*Flower quantity per inflorescence*.—Typically 200 male flowers placed in an average of 1 spikelet and an average of 50 female flowers placed in an average of 1 spikelet.

*Lastingness of inflorescence*.—Flowers last about 10 days.

*Fragrance*.—None.

*Floret buds*.—Ovate in shape, 1.5 cm in length and about 3.5 mm in diameter, range from 144D in color.

*Spikelet aspect*.—Upright to outward.

*Spikelet shape*.—Sedge-like.

*Persistence of spikelets*.—Persistent.

*Floret (spikelet) size*.—Staminate florets; up to 6 cm in length, 5 mm in diameter, pistillate florets; up to 2.5 cm in length, 1.5 cm in diameter.

*Floret (spikelet) description*.—1 glume on outer side and 1 lemma on inner side on staminate florets and 1 lemma on inner side of pistillate florets, glumes; an average of 5 mm in length and 1 mm in width, lanceolate in shape, margin entire, apex narrowly acute, color of upper and lower surface 142C, surface is smooth and dull in appearance, lemma; an average of 2 mm in length and .5 mm in width, lanceolate in shape, margin entire, apex long and mucronate, color of upper and lower surface on staminate florets a blend of 165A and 165B, color of upper and lower surface on pistillate florets 165B, surface is smooth and dull, and lustrous in appearance.

*Peduncle*.—An average of 24.5 cm in length and 4 mm in diameter, very strong, slightly outward angle from vertical, triangular in shape, surface is glossy and 144A in color.

Reproductive Organs:

*Gynoecium*.—Pistils; 3, 7 mm in length, stigmas; fimbriate, 197C in color, style; minute, 0.1 mm in length, insufficient in size to be color coded, ovary; 157A in color.

*Androecium*.—Stamens; 3, basifixed, 2 mm in length, color 164A, pollen; none observed.

*Fruits and seeds*.—Seed production has not been observed to date.

It is claimed:

1. A new and distinct cultivar of *Carex* plant named 'Lunar Falls' as herein illustrated and described.

* * * * *